(12) United States Patent
Poole

(10) Patent No.: US 6,213,971 B1
(45) Date of Patent: Apr. 10, 2001

(54) POWER ASSISTED LIPOSUCTION DEVICE

(76) Inventor: James Poole, P.O. Box 488, Santa Paula, CA (US) 93060-0488

( * ) Notice: Subject to any disclaimer, the term of this patent is extended or adjusted under 35 U.S.C. 154(b) by 0 days.

(21) Appl. No.: 09/185,843

(22) Filed: Nov. 4, 1998

(51) Int. Cl.[7] .............................. A61M 1/00; A61N 1/30
(52) U.S. Cl. .............................. 604/35; 604/19; 604/28; 604/542
(58) Field of Search ....................... 604/540, 542, 604/19–22, 28, 35–38; 128/898; 606/32–41

(56) References Cited

U.S. PATENT DOCUMENTS

| | | | |
|---|---|---|---|
| 5,013,300 | * | 5/1991 | Williams .............................. 604/119 |
| 5,968,007 | * | 10/1999 | Simon et al. ......................... 604/22 |
| 6,007,512 | * | 12/1999 | Hooven .................................. 604/22 |
| 6,013,048 | * | 1/2000 | Podany et al. ......................... 604/22 |
| 6,027,515 | * | 2/2000 | Cimino ................................. 604/169 |

* cited by examiner

Primary Examiner—Angela D. Sykes
Assistant Examiner—Patricia Bianco

(74) Attorney, Agent, or Firm—Riordan & McKinzie; Scott R. Miller, Esq.; Dennis S. Morris, Esq.

(57) ABSTRACT

A method and apparatus is described for performing a liposuction procedure by means of a power-assisted liposuction device. The apparatus comprises a hand-holdable handle assembly (enclosing a gas driven reciprocating piston rod), a detachable cannula, an aspirator pump attached to the hand-holdable handle assembly and a foot pedal assembly that includes a vibrator element for regulating the supply of gas to the hand-holdable handle assembly. The hand-holdable handle assembly generally consists of a barrel, a hollow piston rod which reciprocates relative to the barrel, a seal body, an end cap (having a internal aspirated chamber), an atmospheric access return gallery, and a return spring chamber. Detachably coupled to the hand-holdable handle assembly by means of a quick disconnect is a hollow cannula, the distal end of which contains an aspiration aperture. The foot pedal assembly generally consists of a pedal bell, a metering chamber and a vibrator element, all of which together allow the operator to regulate the flow of gas to the hand-holdable handle assembly, (and, correspondingly, the reciprocation of the hollow piston rod and the hollow cannula) Finally, the hand-holdable handle assembly and the hollow cannula are constructed such that they, together with the necessary tubing, may be easily sterilized.

10 Claims, 8 Drawing Sheets

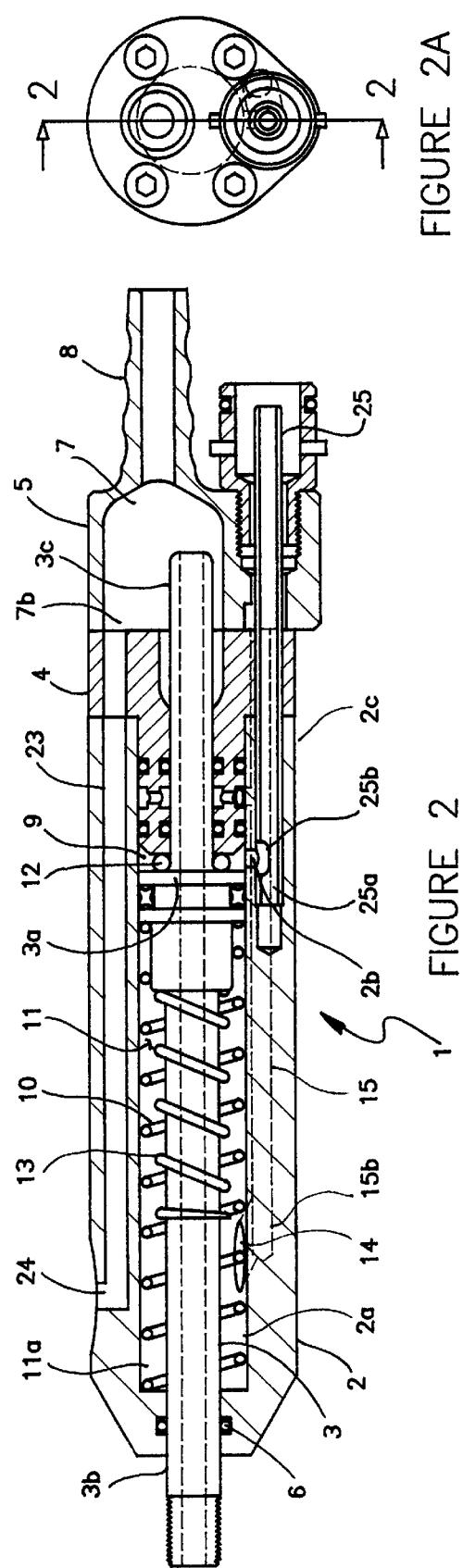
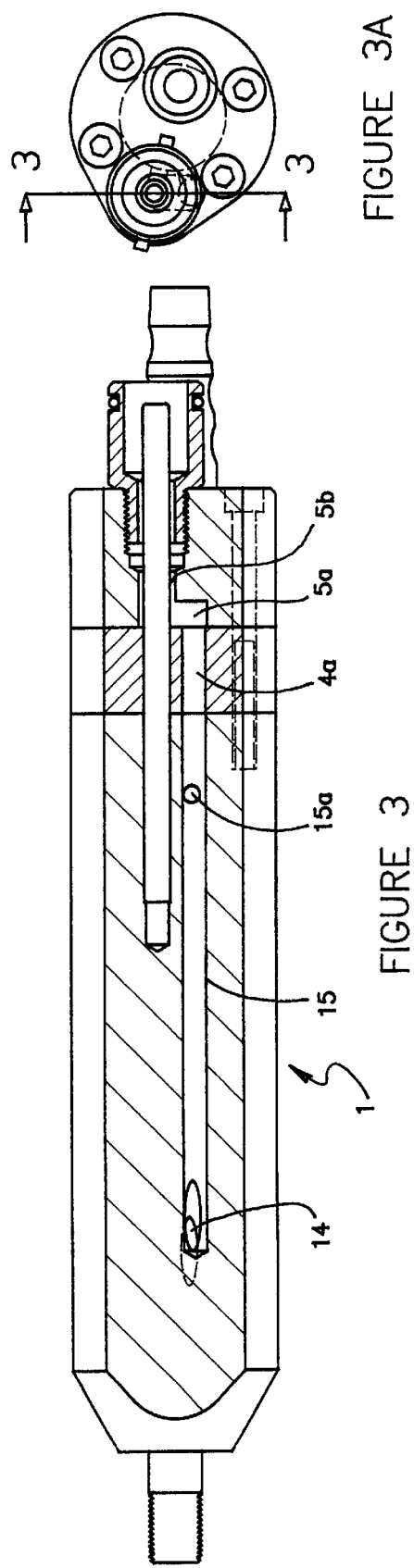

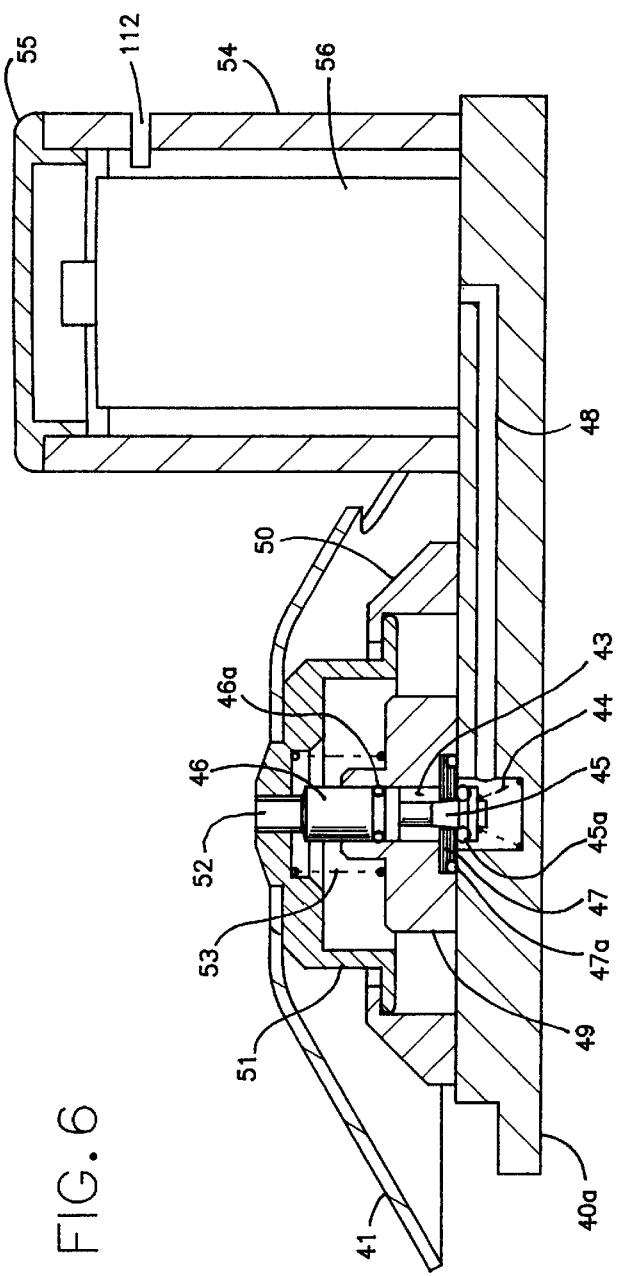
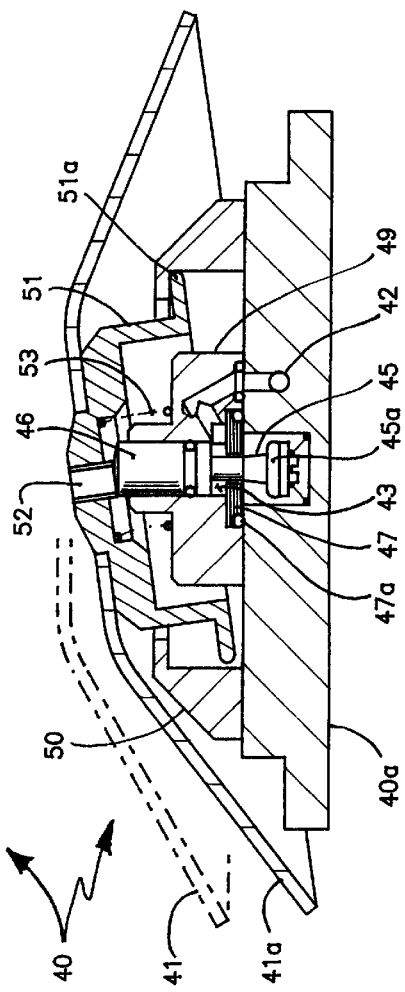
FIG. 6
FIG. 6A

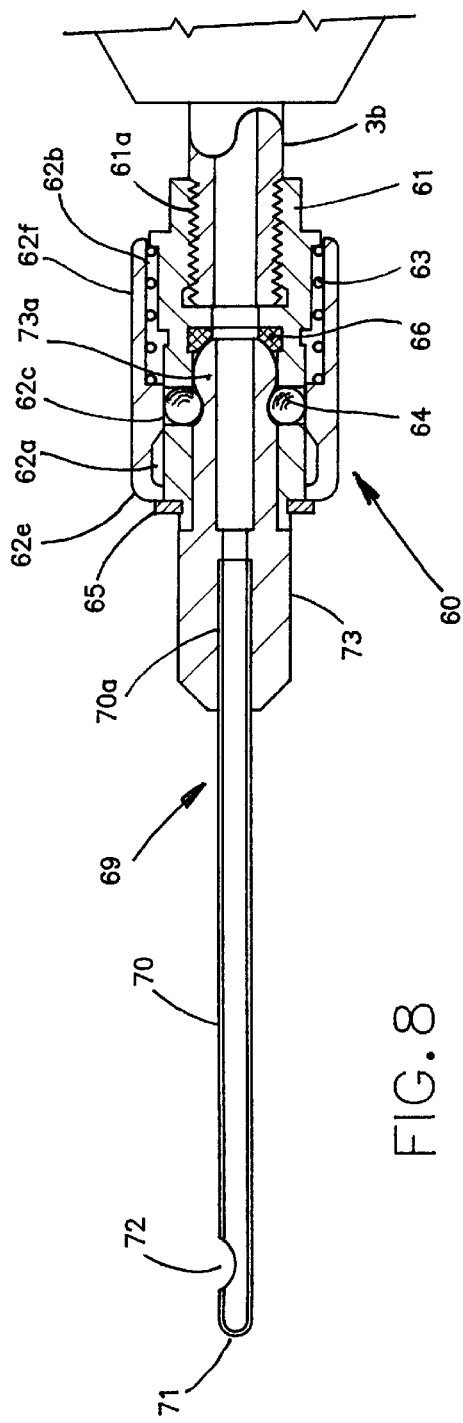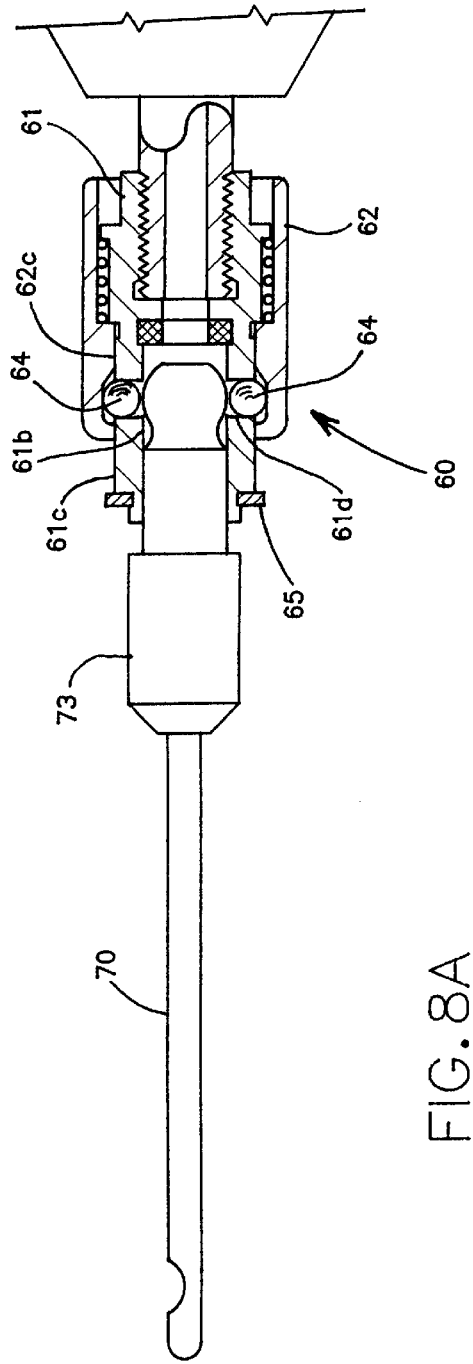
FIG. 8
FIG. 8A

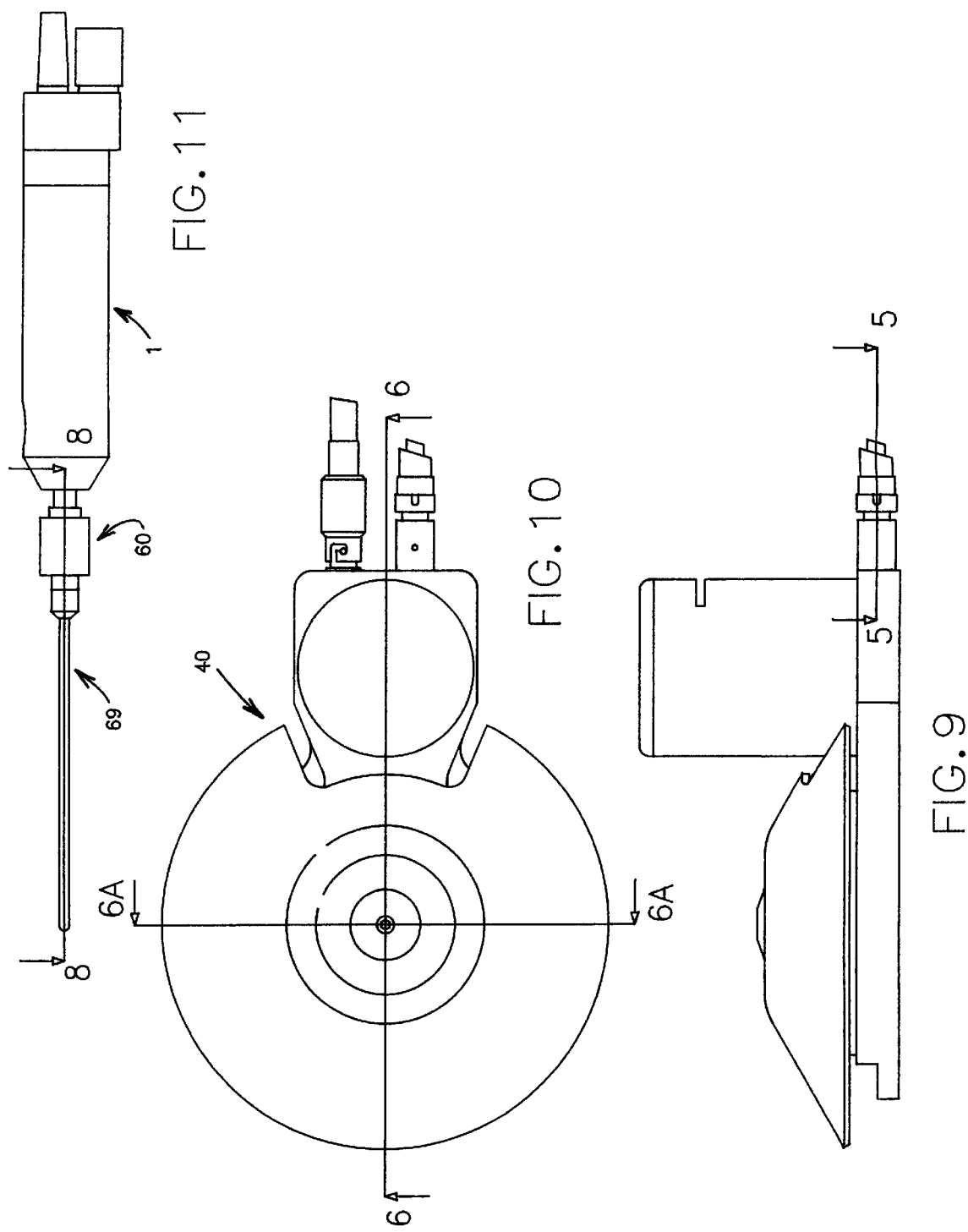

POWER ASSISTED LIPOSUCTION DEVICE

FIELD OF INVENTION

The present invention relates to a method and apparatus for the removal of unwanted fatty tissue (liposuction) through the use of a power-assisted liposuction cannula.

BACKGROUND OF THE INVENTION

Suction-lipectomy, otherwise known as liposuction, is a common surgical procedure used to aesthetically improve the shape of the human form, and is one of the most common body-enhancing procedures performed today. During liposuction, small incisions are made in the area where the procedure is to be performed and a cannula is inserted into the fatty deposits below the skin. The cannula breaks through the fibrous sacks containing the fatty fluids, and said fluids are then suctioned out of the body and through the cannula by means of a vacuum applied to the cannula.

There are currently two distinct methods by which surgeons perform a liposuction procedure. Each requires the surgeon to repeatedly push and pull the cannula to break through the fatty deposits so that the fatty liquids may be suctioned away. The first of the methods is called the "tunneling" procedure, and involves the surgeon making one or two incisions into the fatty tissue of the patient. The cannula is then used to make radial excursions ("tunnels") into the fatty deposits surrounding the incisions. At the area of each of these excursions the fatty liquids are suctioned away by the vacuum applied to the cannula. In the second, original, method of liposuction, an entire layer of deep fat is removed from beneath the skin, which is hopefully naturally followed by skin retraction.

Each of the techniques described above requires the surgeon to manually push and pull, back and forth, the cannula while making the normal twenty to thirty tunnels that are required to remove the necessary amount of fatty tissue. As can be expected, the constant, repeated, pushing and pulling of the cannula by the surgeon is extremely tiring for the surgeon, and limits the duration during which the surgeon can perform liposuction procedures at his optimal performance level. In addition, the procedure is extremely traumatic for the patient, and the patient's skin will typically turn black-and-blue in the affected area for up to several weeks after the procedure. It has been found that the use of a smaller cannula is less traumatic for the patient. The use of a smaller cannula, however, results in greater fatigue for the surgeon, as he is required to make more tunnels to remove the same amount of fatty deposits as would be required with a larger cannula.

To remedy the preceding problems, several different powered liposuction devices have been proposed. U.S. Pat. No. 5,352,194 to Greco et al. provides for a pneumatically driven powered cannula which is controlled by either mechanical abutment means or a series of switches that can be turned on or off to control the stroke length of the cannula. In addition, it is proposed that the cannula be controlled by the modulation of a servo valve, such as by an electronic signal generator or a wave form generator.

U.S. Pat. Nos. 5,348,535 and 5,643,198 to Cucin disclose a cannula assembly that includes an inner and an outer cannula, with each having an aspiration aperture at the distal end such that they are in at least partial registration to form an effective aspiration aperture. During a liposuction procedure, one of the cannulas reciprocates while the other is stationary relative to the housing. The reciprocation of the cannula is achieved by means of either a gas driven piston-type motor, the travel of which is manually controlled by moving a sliding member extending from the hand-holdable housing, or by manually adjusting by hand the amount of gas driving the piston-type motor.

Various problems exist, however, with these prior liposuction devices. In particular, it is difficult to regulate the stroke length and rate of the cannula, as the surgeon must interrupt the procedure each time he wishes to adjust the reciprocation of the cannula. In addition, in neither of the above devices is the stroke length of the cannula tied to the stroke rate, such that the greater the length of the stroke the slower the stroke rate. Tying the stroke length of the cannula to the stroke rate provides greater safety for the patient, especially when performing liposuction procedures in particularly sensitive areas of the body such as the face and neck, and also provides greater ease of use for the surgeon. Furthermore, none of the prior cannulas allow for the easy sterilization of the entire hand-holdable handle assembly and cannula.

Accordingly, it is the object of the present invention to provide a power-assisted liposuction device to assist the surgeon in performing liposuction procedures with greater control and less fatigue.

It is correspondingly an object of the present invention to provide a power-assisted liposuction device to enhance the safety of the patient, both through easing the fatigue of the surgeon, and connecting the stroke length of the cannula to the stroke rate such that the longer the stroke length of the cannula the slower its stroke rate.

It is a further object of the present invention to provide for a power-assisted liposuction device in which the cannula reciprocates relative to the hand-holdable handle assembly by means of a piston rod driven by compressed gas.

It is still a further object of the present invention to allow the stroke length and correspondingly the stroke rate to be easily adjustable, and for the adjustment to be able to be made without the surgeon needing to interrupt the liposuction procedure.

It is another object of the present invention to construct the power assisted liposuction device such that any part of said device that must be sterilized, including the cannula, its connection to the hand-holdable handle assembly, and the hand-holdable handle assembly itself are able to be easily sterilized, and can be sterilized without the need to disassemble the entire said device.

An even further object of the present invention is to attach the cannula to the hand-holdable handle assembly by means that allow for the easy and quick changing of cannulas during a liposuction procedure or for purposes of sterilization.

These and other objects and uses of the present invention will become apparent upon consideration of the description that follows.

SUMMARY OF THE INVENTION

The present invention provides a power-assisted liposuction device in which the reciprocation of the cannula relative to the hand-holdable handle assembly is mechanically automated, and in which the stroke length of the cannula is inversely proportional to its stroke rate. Generally, the device consists of a cannula, a hand-holdable handle assembly, and a foot pedal assembly that contains a vibrator element for regulating the flow of gas to the hand-holdable handle assembly.

Mechanically assisting the reciprocation of the cannula will greatly ease the fatigue of the surgeon, and regulating the stroke length of the cannula according to its stroke rate will greatly enhance both the comfort and safety of the patient. In addition, automating the reciprocation of the cannula will allow for the use of smaller cannulas, and will again provide for greater safety and comfort for the patient, as well as allowing for a more exacting procedure that heals more quickly than with the use of a non-powered cannula. Finally, the present design also allows for the easy sterilization of any part of the power assisted liposuction device that must be sterilized.

BRIEF DESCRIPTION OF THE DRAWINGS

FIG. 2 is a cross sectional side view of the hand-holdable handle assembly shown along line 2—2 of FIG. 2A.

FIG. 2A is an end view of the hand-holdable handle assembly.

FIG. 3 is a cross sectional side view of the hand-holdable handle assembly shown along line 3—3 of FIG. 3A.

FIG. 3A shows an end view of the hand-holdable handle assembly.

FIG. 5A is a cross sectional top view along line 5—5 of FIG. 9 illustrating the gas supply tube coupling at its connection to the foot pedal assembly with the valve shutting off the gas supply from the tank.

FIG. 6 is a cross sectional side view taken along line 6—6 of FIG. 10 illustrating the foot pedal assembly and the vibrator element.

FIG. 6A is a cross sectional side view taken along line 6A—6A of FIG. 10 of the foot pedal assembly with the pedal bell depressed.

FIG. 8 is a cross sectional side view taken along line 8—8 of FIG. 11 illustrating the hollow cannula and the quick disconnect.

FIG. 8A is a cross sectional side view taken along line 8—8 of FIG. 11 illustrating the hollow cannula and quick disconnect with the hollow cannula partially removed from the quick disconnect.

FIG. 9 is a side view of the foot pedal assembly.

FIG. 10 is a top view of the foot pedal assembly.

FIG. 11 is a side view of the hand-holdable handle assembly and cannula.

DETAILED DESCRIPTION

Figure 1:
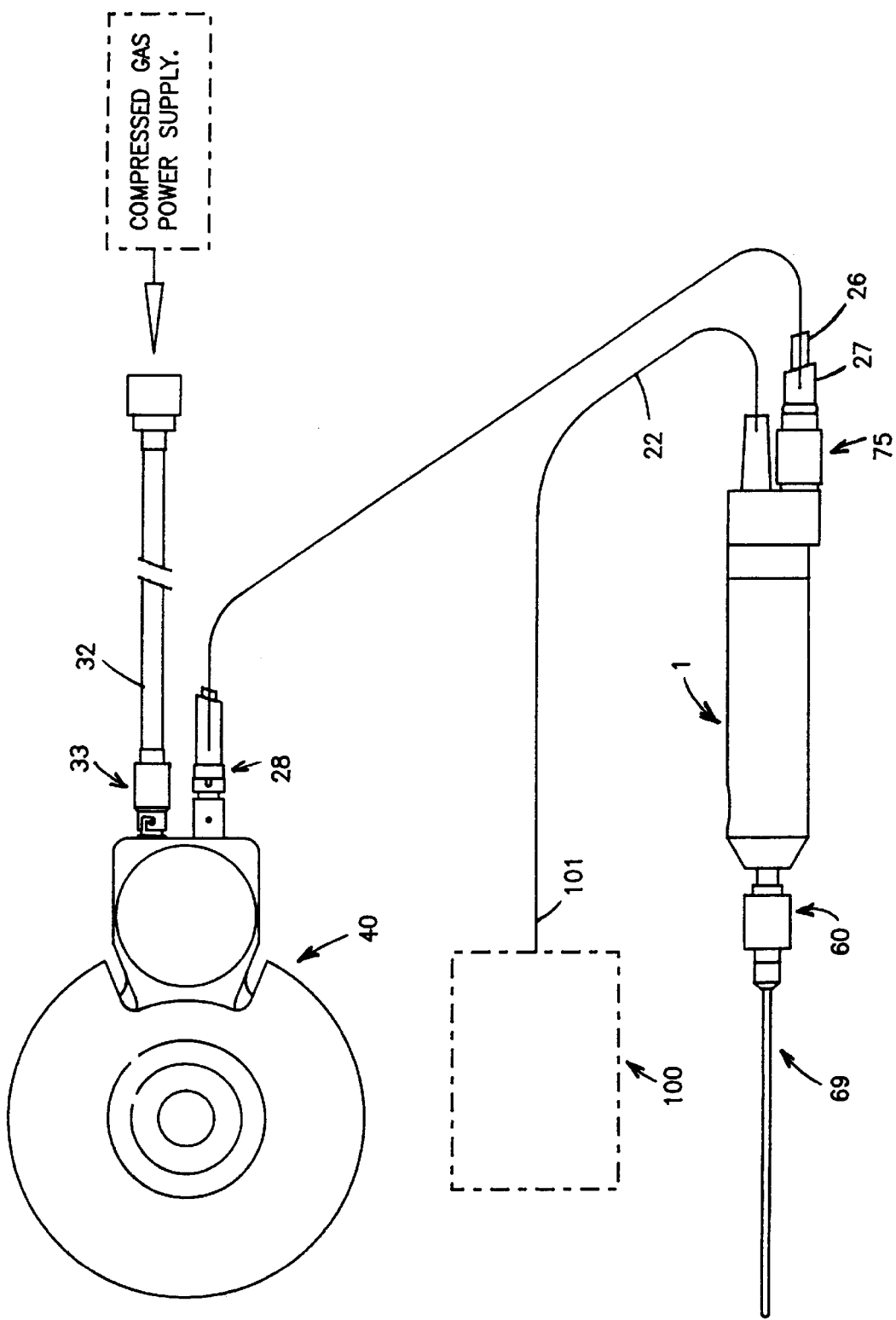
FIG. 1 is a non-detailed illustration of the entire power assisted liposuction device.

As depicted in FIG. 1, in general, the power assisted liposuction device described herein contains a hand-holdable handle assembly 1 (enclosing a gas driven reciprocating piston rod), a detachable cannula 69, and a foot pedal control assembly 40 that includes a vibrator element for regulating the supply of gas to the hand-holdable handle assembly 1. This assembly allows for the power-assisted cannula to be controlled such that the faster the stoke rate of the cannula, the shorter the stroke length of the cannula.

Figure 4:
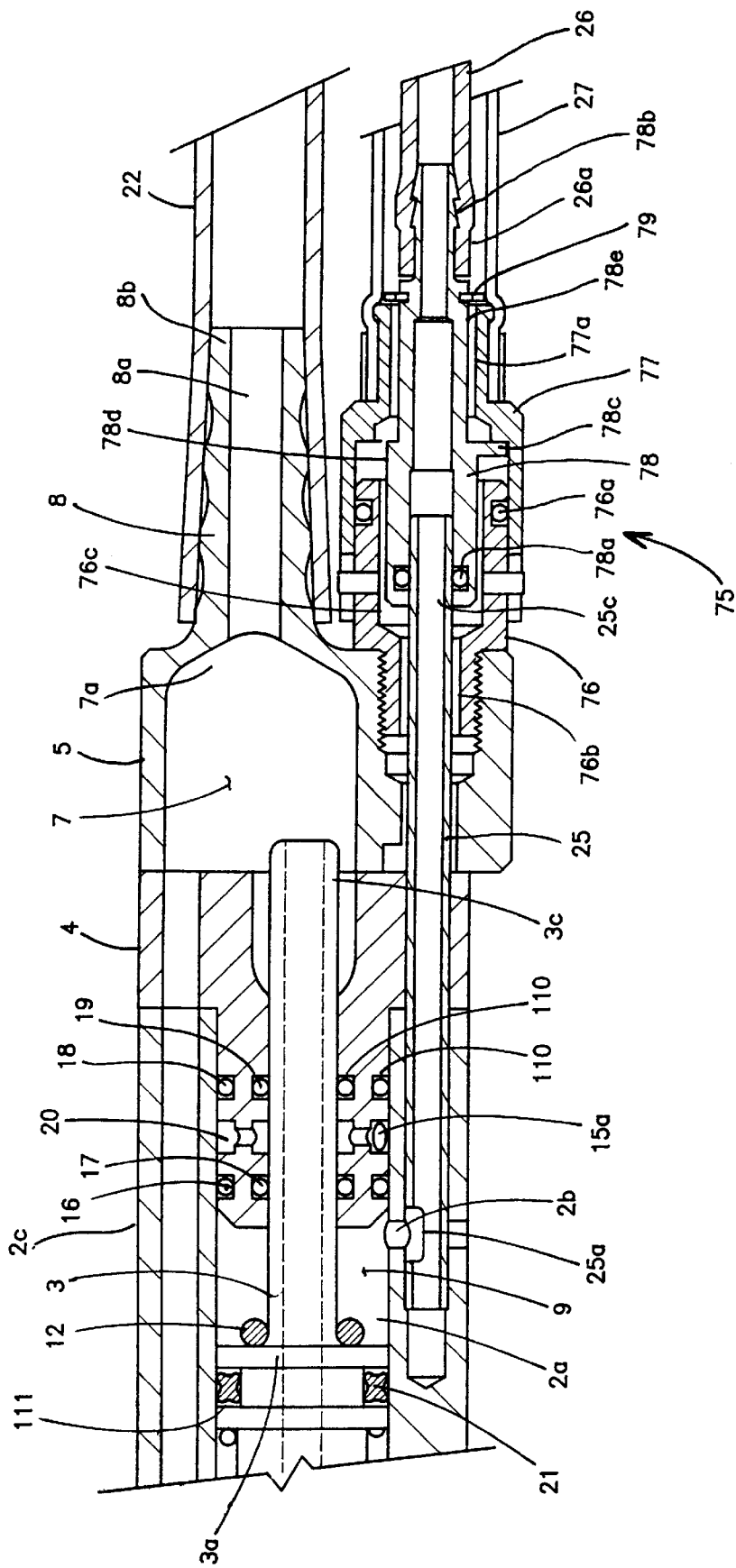
FIG. 4 is an enlarged view of a portion of FIG. 2 also showing the hand-holdable handle assembly connected to gas supply and suction tubes.

As illustrated in greater detail in FIG. 2, hand-holdable handle assembly 1 generally consists of a cylindrical barrel 2, a hollow piston rod 3, a seal body 4, an end cap 5 (having an internal aspirated chamber 7), a vent hole 15 and a return spring chamber 11. More specifically, as depicted in FIG. 2, handle assembly 1 consists of cylindrical barrel 2 with inner bore 2a. Within inner bore 2a is hollow piston rod 3. Distal end 3b of hollow piston rod 3 is sealed at the location of its protrusion from cylindrical barrel 2 by means of O-ring type seal 6. As depicted in FIG. 8, coupled to distal end 3b of hollow piston rod 3 by quick disconnect 60 is hollow cannula 70. As depicted in FIG. 2, proximal end 3c of hollow piston rod 3 passes through seal body 4 and terminates in aspirated vacuum chamber 7 of end cap 5. All fatty liquids removed from the body during a liposuction procedure are forced by means of a vacuum through hollow cannula 70 through quick disconnect 60, and then through hollow piston rod 3, into aspirated vacuum chamber 7. Said fatty liquids are then evacuated from the vacuum chamber 7 by means of a hose 22 (FIG. 4). As best illustrated in FIG. 1, one end of the hose 22 is connected to an aspirator vacuum pump 100; the other end is detachably coupled to boss 8 of end cap 5, which is also depicted in detail in FIGS. 2 and 4.

As shown in FIG. 4, hollow piston rod 3 reciprocates in inner bore 2a of cylindrical barrel 2 by means of pressure exerted against the backward end of piston 3a, said pressure being supplied by means of a gas, such as nitrogen, which is forcibly injected into hollow area 9 located behind the backward end of piston 3a, and which forces the forward movement of hollow piston rod 3 relative to cylindrical barrel 2. Pressured gas is directed to hollow area 9 by inlet gas supply tube 25 which is attached to back end 2c of cylindrical barrel 2. Forward end 25b of inlet gas supply tube 25 is preferably notched, as shown at 25a, said notch being in line with hole 2b leading to hollow area 9. Inlet gas supply tube 25 passes through seal body 4 and end cap 5, and at its proximal end 25c terminates in seal 78A in tube connector 75.

As depicted in FIG. 2, after hollow piston rod 3 has been forced into a forward position, it is returned to a backward position by means of piston rod return spring 10 located within return spring chamber 11. Upon being forcibly returned to a backward position by means of piston rod return spring 10, hollow piston rod 3 travels until the backward travel of piston 3a is forcibly halted by O-ring type return stroke buffer 12 which sits on hollow piston rod 3 at the base of piston 3a. Also contained within return spring chamber 11 is overtravel buffer spring 13. Overtravel buffer spring 13 is a spring of greater strength than piston rod return spring 10, and functions so that if piston rod return spring 10 were to fail to arrest the forward movement of hollow piston rod 3, overtravel return spring 13 would arrest the forward movement of said hollow piston rod 3 before the proximal end of hollow piston rod 3 passed beyond the seals in seal body 4 and into hollow area 9, thus preventing the entrance of gas into the center bore of hollow piston rod 3.

Figure 5:
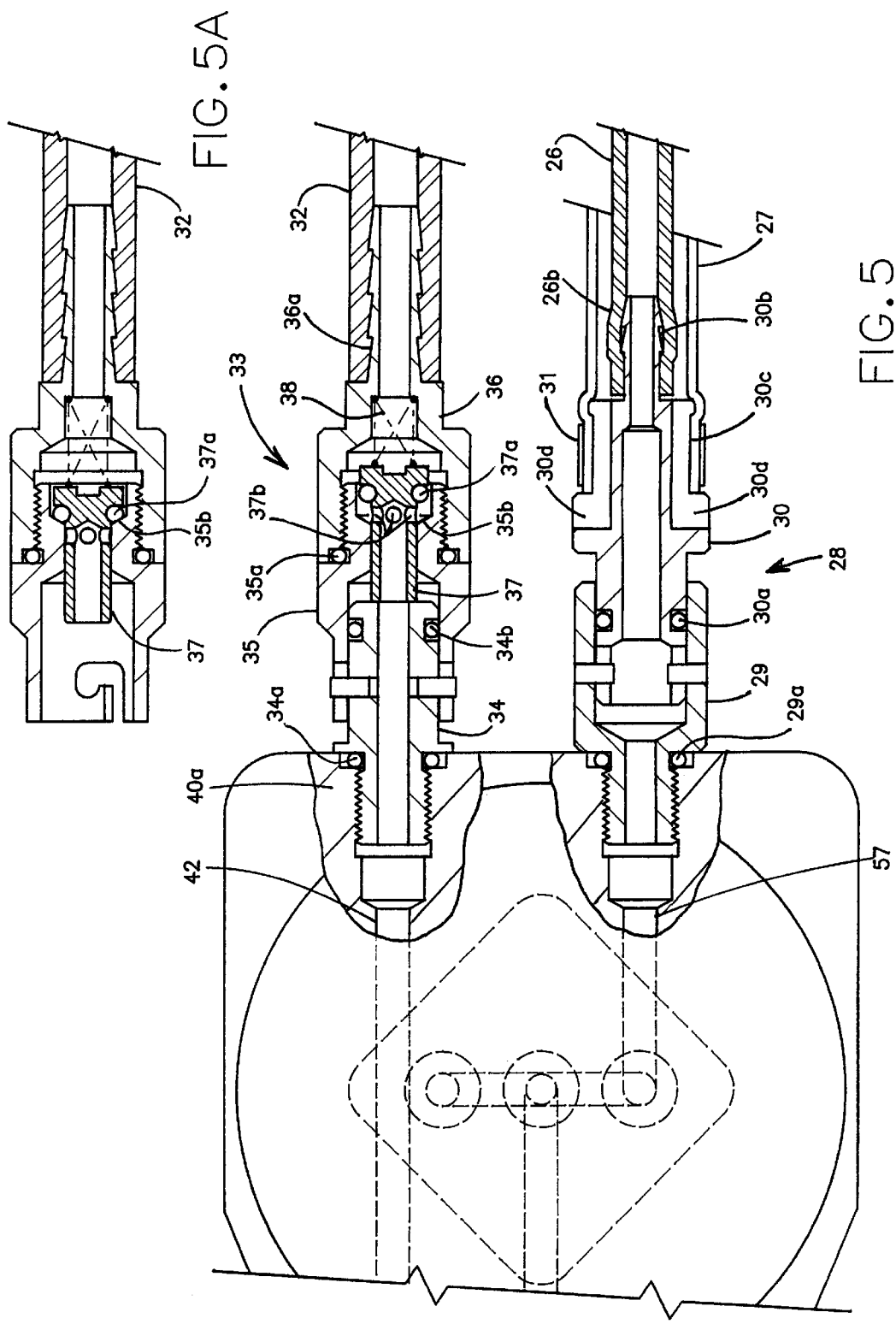
FIG. 5 is a partial cross sectional top view along lines 5—5 of FIG. 9 illustrating the manner in which the atmospheric access tube and gas supply tubes are connected to the foot pedal assembly.
Figure 7:
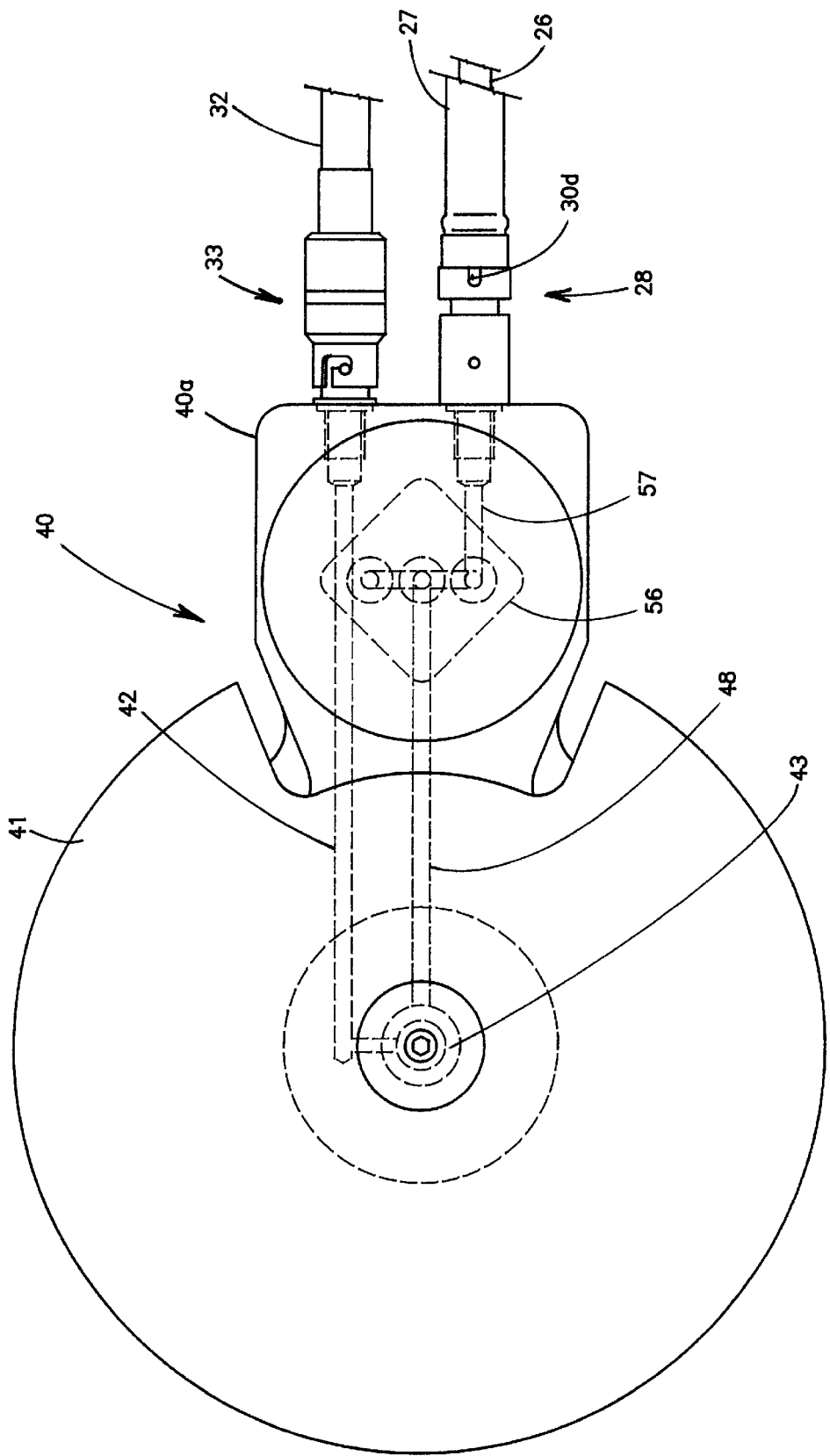
FIG. 7 is a top view illustrating the foot pedal assembly and the vibrator element.

Referring to FIGS. 2–4, parallel to inner bore 2a (and within the wall of cylindrical barrel 2) is vent hole 15. Extending from distal end 15b of vent hole 15 is pathway 14 which enters into inner bore 2a in forward end 11a of return spring chamber 11. Aligned with evacuation gallery 20 of seal body 4 is access hole 15A connecting inner bore 2a to vent hole 15. At its proximal end, vent hole 15 is aligned with hole 4a extending through seal body 4, said hole 4a thereafter being aligned with cavity 5a in end cap 5, and then connected to hole 5b in end cap 5. Air in return spring chamber 11 that is displaced by the forward movement of piston 33a travels through pathway 14 to vent hole 15 to hole 4a to cavity 5a and finally to hole 5b in end cap 5. After said gas has passed through hole 5b, it travels through the inside diameter of male cylindrical body 76, a component of coupling 75, to tube 27 until it is finally released to the atmosphere through slots 30d in coupling 28, as best shown in FIG. 5.

As depicted in FIG. 4, a cylindrical seal body 4 is insertably secured (for example, with screws) to proximal end 2c of cylindrical barrel 2 in front of end cap 5. Seal body 4 also contains primary O-ring seals 16 and 17, secondary O-ring seals 18 and 19 and primary seal leak evacuation gallery 20. Seal body 4, primary seals 16 and 17, secondary seals 18 and 19 and primary seal leak evacuation gallery 20 act to assure that no gas forcibly inserted into hollow area 9 at the base of piston 3a is able to enter into aspirated chamber 7. The primary and secondary seals are preferably constructed from a combination of annular grooves 110 on the outside and inside diameters of seal body 4, with an O-ring placed in such grooves so as to form a seal when seal body 4 is insertably coupled to cylindrical barrel 2. Primary seals 16 and 17 are conventional O-ring type seals which function to assure that no gas entering into hollow area 9 is able to travel into aspirated chamber 7. Primary seal leak evacuation gallery 20 assures that any gas that passes beyond primary seals 16 and 17 enters into primary seal leak evacuation gallery 20 and then passes through access hole 15a into gallery 15 and through coupling 75 to hose 27, and thereafter out to atmosphere at slots 30d (See e. g., FIG. 5). Similarly, secondary seals 18 and 19 are conventional O-ring type seals which serve to assure that any gas that has passed beyond primary seals 16 and 17 may only escape through primary seal leak evacuation gallery 20, and is not permitted to enter into aspirated chamber 7. In addition, piston 3a contains an annular groove 111 into which piston seal 21, an O-ring type seal, is inserted to stop any gas from passing from hollow chamber 9 into return spring chamber 11.

As described above, proximal end 3c of hollow piston rod 3 terminates in aspirated chamber 7, and all fatty liquids removed from the body are suctioned through hollow cannula 70 and hollow piston rod 3 into aspirated chamber 7 by means of a vacuum aspirator 100. For this purpose, as depicted in FIG. 4, backward end 7a of aspirated chamber 7 connects to bore 8a in end cap 5 which is bored through hose accepting boss 8. Coupled to the proximal end 8b of hose accepting boss 8 is aspirator hose 22, through which suction is applied to aspirated chamber 7, thereby causing all fatty liquids which the surgeon desires to remove from the body to travel through hollow cannula 70 and hollow piston rod 3, into aspirated chamber 7 and through aspirator hose 22 until said fatty liquids are removed at proximal end 101 of aspirator hose 22, attached to vacuum aspirator pump 100, such as that sold by Wells-Johnson, as seen in FIG. 1.

As further depicted in FIG. 2, longitudinally extending from upper portion 7b of aspirated chamber 7 is aspirated chamber vacuum control gallery 23 which terminates at aspirated chamber vacuum control hole 24. Said aspirated chamber vacuum control hole 24 allows the surgeon to control the amount of vacuum being directed through hollow cannula 70, by the surgeon simply covering aspirated chamber vacuum control hole 24 with his or her thumb. When the surgeon's thumb is covering aspirated chamber vacuum control hole 24, the vacuum in aspirated chamber 7 is maintained, and suction is directed along hollow piston rod 3 and hollow cannula 70, thereby causing the removal of fatty liquids from the body. When, however, the surgeon removes his or her thumb from aspirated chamber vacuum control hole 24, the vacuum in aspirated chamber 7 is lessened by atmospheric air being drawn along aspirated chamber vacuum control gallery 23, thereby lessening any vacuum being directed along hollow piston rod 3.

As depicted in FIGS. 8 and 8A, detachably coupled to handle assembly 1 by means of quick disconnect 60 is detachable hollow cannula 70 with a distal end 71, said distal end 71 having an aspiration aperture, as shown at 72. Proximal end 70a of hollow cannula 70 is integral with hollow cannula base 73, and is connected to handle assembly 1 by the insertion of hollow cannula base 73 into quick disconnect 60. Proximal end 73a of said hollow cannula base 73 is spherically shaped, which facilitates the insertion and locking of hollow cannula base 73 into quick disconnect 60.

Quick disconnect 60 consists of cylindrical body 61 that has at its proximal end threads 61a which allow quick disconnect 60 to be attached to the distal end of hollow piston rod 3. The proximal end of cylindrical body 61 has an inner diameter 61b and an outer diameter 61c connected by three radial holes 61d (only two of which are shown in FIG. 8) said radial holes 61d each containing a steel ball 64. Each of radial holes 61d is machined such that steel balls 64 cannot fall into inner diameter 61b of cylindrical body 61. Concentrically fitted to outer diameter 61c of cylindrical body 61 is inner diameter 62c of outer cylindrical sleeve 62. Machined in inner diameter 62c of outer cylindrical sleeve 62 at its distal end 62e is annular groove 62a, and machined in outer cylindrical sleeve 62 at proximal end 62f is inner diameter 62b, in which is located coil spring 63. Coil Spring 63 forces outer cylindrical sleeve 62 forward against retaining clip 65, but allows outer cylindrical sleeve 62 to be manually moved backward. With outer cylindrical sleeve 62 held against retaining clip 65 by coil spring 63, inner diameter 62c of outer cylindrical sleeve 62 forces steel balls 64 inward against the inner diameter of spherical cannula end 73a, locking hollow cannula 70 into quick disconnect 60. Cannula base 73 is sealed from the atmosphere by means of circular seal 66. Hollow cannula 70 is removed (or inserted) into cannula quick disconnect 60 by manually moving backward cylindrical sleeve 62 against coil spring 63 allowing steel balls 64 to move outward into annular groove 62a, thereby unlocking spherical cannula end 73a. FIG. 8A shows hollow cannula 70 partially removed. After fully inserting cannula base 73, coil spring 63 forces cylindrical sleeve 62 forward against retaining clip 65 and steel balls 64 are forced inward and locked against spherical cannula end 73a by cylindrical sleeve inner diameter 62c.

Gas is supplied to inlet gas supply tube 25 through pressure tube 26, distal end 26a of pressure tube 26 being coupled to inlet gas supply tube 25 (See e.g., FIG. 4), and proximal end 26b of pressure tube 26 being detachably coupled to pedal assembly 30 (See e.g., FIG. 5). Pressure tube 26 is located within atmospheric access tube 27, and is detachably coupled to inlet gas supply tube 25 by bayonet type connection 75.

Pressure tube 26 is detachably coupled to inlet gas supply tube 25, and is located within atmospheric access tube 27, such that pressure tube 26 runs for its entire length inside atmospheric access tube 27, from its connection via coupling 75 to inlet gas supply tube 25, until said pressure tube 26 terminates at coupling 28 on foot pedal assembly 40. Pressure tube 26 is connected to hose barb 30b. Gas pulses entering pressure tube 26 at coupling 28 are thus directed to coupling 75 where pressure tube 26 is attached to tube barb 78b of inner body 78 (FIG. 4).

Coupling 75 is a bayonet type coupling consisting primarily of male cylindrical body 76, outer cylindrical sleeve 77 and cylindrical center body 78. More specifically, as depicted in FIG. 4, male cylindrical body 76 is coupled, as by threads, to the back end of end cap 5. Located within annular grove 76b in male cylindrical body 76 is O-ring 76a which seals the inside bore of cylindrical sleeve 77 when male cylindrical body 76 and outer cylindrical sleeve 77 are coupled. Fitted inside outer cylindrical sleeve 77 is center body 78 which is concentrically located by three radial flange arms 78c, and is held in outer cylindrical sleeve 77 by retaining clip 79 seated in a groove in the back end of center body 78. At forward end 78e of center body 78 is O-ring seal 78a located in an annular groove in the inside bore of center body 78. O-ring 78a seals center body 78 to inlet gas supply tube 25.

Gas pulses in pressure tube 26 pass through center body 78 into inlet gas supply tube 25. As described previously, air in return spring chamber 11 displaced by the forward movement of piston 3a is channeled to hole 5b in end cap 5. Said displaced air in hole 5b enters hole 76b, around the outside diameter of inlet gas supply tube 25, to then travel into bore 76c and around outside diameter 78d then around radial flange arms 78c into the gap between diameter 78e and 77a through the openings in retaining clip 79 and finally into atmospheric access tube 27 and thereafter to atmospheric air escape slots 30d in foot pedal control assembly 40.

Although pressure tube 26 is located within atmospheric access tube 27, the atmospheric air that is forced by the reciprocation of piston rod 3 into vent hole 15 through coupling 75 and then into atmospheric access tube 27, is able to travel along atmospheric access tube 27, around the outside of pressure tube 26, until said atmospheric air is finally released into the atmosphere at atmospheric air escape slots 30d.

As depicted in FIG. 6, foot pedal control assembly 40 generally consists of a foot pedal assembly with metering chamber 43 and vibrator element 56 which together act as a valve to regulate the flow of gas that enters handle assembly 1, and thus ultimately acts to drive the reciprocation of cannula assembly 69. In the preferred embodiment foot pedal assembly 40 functions such that the greater the flow of gas to the vibrator element the slower and longer the stroke length of hollow cannula assembly 69, while the less the flow of gas the faster and shorter the stroke length. In this manner the physician is able to easily control the stroke rate and stroke length of hollow cannula 70 and is able to do so in a manner that provides the greatest safety and comfort for the patient.

As depicted in detail in FIG. 6A, the foot pedal assembly has a pedal bell 41. Orifice disk 47, metering needle 45 and plunger 46, are housed in valve body 49 which is attached, as by screws, to pedal base 40a. The above described pedal base assembly 40a and valve body 49 together with pedal bell 41 act to regulate the flow of compressed gas which enters vibrator element 56. The top of metering needle 45 is screwed into the bottom of plunger 46, which has an exterior annular groove into which O-ring seal 46a is placed to seal plunger 46 in valve body 49. Metering needle 45 extends through orifice disk 47, said orifice disk 47 having O-ring seal 47a at its outer edge to prevent the escape of any gas from metering chamber 43. In addition, O-ring seal 45a at the bottom of metering needle 45 acts to seal metering needle 45 against the underside of orifice disk 47. After said compressed gas enters foot pedal base 40a, it is channeled through gallery hole 42 to metering chamber 43, which contains metering needle 45 inside orifice disk 47. Attached to the upper end of metering needle 45 is plunger 46, which acts to depress metering needle 45 when pedal bell 41 is forced down, as by the surgeon's foot during a liposuction procedure.

Pedal bell 41 is optimally made such that the surgeon is able to step on any part of the bell and regulate the flow of pressured gas to vibrator element 56. To this end, pedal bell 41 is attached, as by screws, to hinge cap 51, which is retained by hinge ring 50, which in turn is attached as by screws, to pedal base 40a. Positioned between the top of valve body 49 and the underside of hinge cap 51 is coil spring 53 which returns pedal bell 41 to its horizontal at-rest position when the pressure applied to pedal bell 41, as by the surgeon's foot, is released. Adjustable set screw 52 is positioned in the top center of hinge cap 51 such that when pedal bell 41 is stepped on at its outer perimeter 41a it rotates about hinge part 51a. Since all components are diametrical in shape, the same result is obtained no matter which portion of the outer edge of pedal bell 41 is stepped on. In addition, set screw 52 is positioned in the center of hinge cap 51 and adjusts so that O-ring 45a seals against the underside of orifice disk 47, and so that the full travel of needle 45 may be maintained. When metering needle 45 is depressed by the surgeon stepping on pedal bell 41, orifice 47 progressively opens and allows pressurized gas to be channeled along gallery hole 48 to vibrator element 56. When the surgeon either removes his foot from the pedal bell, or lessens the pressure applied to said pedal bell, spring 53 and conical compression spring 44 progressively return metering needle 45 to an upward position, at which time O-ring type seal 45a on the bottom of metering needle 45 contacts the underside of orifice disk 47, thus closing the orifice, and thereby closing off the flow of pressurized gas into gallery hole 48 and thereafter into vibrator element 56.

Vibrator element 56 is a commercially available device, such as that manufactured by Aro Corp., Model No. 59890, and functions such that when said vibrator element is supplied with gas at a constant pressure through gallery hole 48 and said pressurized gas has been channeled through said vibrator element, the gas exiting from said vibrator element consists of timed pulses, said timed pulses being at the same pressure as when said pressurized gas entered vibrator element 56. The gas pulses from vibrator element 56 are directed through gallery hole 57 in foot pedal base 40a to outlet coupling 28 and then through said outlet coupling 28 to pressure tube 26 and thereafter to handle assembly 1 and are used to drive the forward motion of hollow piston rod 3. Outlet coupling 28 is a bayonet type coupling consisting primarily of two components, 29 and 30. Female cylindrical body 29 is coupled, as by threads, to foot pedal base 40a and sealed by O-ring 29a.

Inserted into female cylindrical body 29 and sealed by O-ring 30a is male cylindrical body 30. Gas pulses flow through female cylindrical body 29 and male cylindrical body 30 into pressure tube 26, which is attached to barb 30b of male cylindrical body 30. As depicted in FIG. 6, muffler tube 54 and muffler cap 55 are attached, as by screws to pedal base 40a. Gas pulses exhausted through the side of vibrator 56 expand inside of said muffler tube 54 and escape to the atmosphere through slot 112. When the supply of pressurized gas to vibrator element 56 is terminated, said vibrator element immediately ceases to produce timed pulses of gas, and the reciprocal movement of piston rod 3 likewise immediately ceases, and piston rod 3 returns to a retracted position by means of return spring 10. After the reciprocal movement of piston rod 3 has ceased, detachable hollow cannula 70 may be used by the surgeon in the standard manual manner. Atmospheric access tube 27 is attached by ferrule 31 to outer diameter 30c of male cylindrical body 30, said outer diameter 30c having two slots 30d allowing access to atmosphere for atmospheric access tube 27.

As depicted in FIG. 5, gas at constant pressure is directed by hose 32 to inlet coupling 33, (see also FIGS. 1 and 5A). Coupling 33 is a bayonet type coupling which automatically shuts off when the female part of the coupling is detached from the male portion thereof. FIG. 5A shows coupling 33 disconnected (i.e., gas supply shut-off). Hose 32 is attached to hose barb 36a. The backward female portion 36 of coupling 33 is attached by thread to the forward female portion 35 of coupling 33 and sealed by O-ring 35a. Valve 37 is located inside forward female portion 35, and O-ring 37a is pushed by spring 38 and gas pressure against face 35b stopping gas flow at that point.

Body 34 is attached, as by threads, to foot pedal base 40a (See e.g., FIG. 5) and sealed by O-ring 34a. Located within an annular groove in body 34 is O-ring 34b which seals male member 34 of coupling 33 inside female member 35 thereof. When forward female portion 35 is coupled to male member 34 the forward end of male member 34 pushes valve 37 back against spring 38, which also moves O-ring 37a off seal face 35b allowing gas to flow through holes 37b into the inside bore of male member valve 37, and thereafter through the center bore of male member 34 and into pedal gallery hole 42. While described in reference to the above identified components, the present invention can be used with other and different configurations which will be known to those skilled in the art. Thus, the present invention is limited only by the claims set forth below.

What is claimed is:

1. A power assisted liposuction device comprising:
   a hand-holdable handle assembly, said handle assembly operably connected to a reciprocating piston;
   a hollow cannula detachably connected to said hand-holdable handle assembly;
   a valve means, said valve means connected to said reciprocating piston for controlling actuation of said reciprocating piston; and
   a foot pedal assembly, said foot pedal assembly including a metering chamber which controls stroke oscillation of said hollow cannula by varying gas pressure from a gas supply to said reciprocating piston.

2. A power assisted liposuction device as set forth in claim 1 wherein said foot pedal assembly includes a vibrator element for creating variable pulses of gas to act on said reciprocating piston.

3. A power assisted liposuction device as set forth in claim 2 further including a quick disconnect detachably coupled to said hollow cannula whereby displacement of said quick disconnect will either cause said hollow cannula to tighten onto or release from said hand-holdable handle assembly.

4. A power assisted liposuction device as set forth in claim 2 wherein said reciprocating piston is mounted within the hand-holdable handle assembly.

5. A power assisted liposuction device as set forth in claim 1 further including a quick disconnect detachably coupled to said hollow cannula whereby displacement of said quick disconnect will either cause said hollow cannula to tighten onto or release from said hand-holdable handle assembly.

6. A power assisted liposuction device as set forth in claim 1 wherein said reciprocating piston is mounted within the hand-holdable handle assembly.

7. A method for operating a liposuction cannula comprising, actuating a reciprocating piston connected to a foot pedal assembly having a metering chamber for controlling the flow of gas from a means for providing gas to said reciprocating piston thereby creating pressure resulting in actuation, said reciprocating piston mounted within a hand-holdable handle assembly connected to said cannula, said cannula having a distal end and a base end, whereby said actuating of said piston causes said cannula to reciprocate; controlling power assisted liposuction procedure such that the longer the stroke length of the cannula the slower the stroke rate of the cannula; and inserting said cannula into a human body for removing fatty tissue where fatty tissue is freed and passes through said cannula by virtue of reciprocation created by said reciprocating piston.

8. The method as set forth claim 7 wherein said foot pedal assembly further comprises a vibrator element.

9. A liposuction device comprising:
   means for providing power to said liposuction device; and
   a foot pedal assembly having a metering chamber as part of said foot pedal assembly for controlling the provision of power to said liposuction device.

10. A power assisted liposuction device comprising:
    a hand-holdable handle assembly;
    a reciprocating piston assembly connected to said hand-holdable handle assembly;
    a detachable hollow cannula detachably connected to said hand-holdable handle assembly;
    a valve means for controlling the actuation of said piston assembly mechanically connected to said piston assembly and said hollow cannula whereby actuation of said piston assembly results in relative reciprocation of said hand-holdable handle assembly and said hollow cannula; and
    a foot pedal assembly, said foot pedal assembly including a metering chamber which controls stroke oscillation of said hollow cannula by varying gas pressure from a gas supply to said reciprocating piston for performing a power assisted liposuction procedure wherein the longer the stroke length of the cannula the slower the stroke rate of the cannula.

* * * * *